United States Patent [19]

Moriwaki et al.

[11] Patent Number: 5,489,625
[45] Date of Patent: Feb. 6, 1996

[54] DENTAL ADHESIVE COATING BASE COMPOSITION AND ORAL COMPOSITION

[75] Inventors: Yutaka Moriwaki, Wakayama; Yujiro Uchiyama; Akio Tani, both of Osaka; Shigeaki Matsumoto, Nara; Hiroshi Furumichi; Takao Makishima, both of Osaka; Kiyoshi Maekawa, Shiga, all of Japan

[73] Assignees: Sunstar Kabushiki Kaisha; Osaka Organic Chemical Industries Co., Ltd., both of Osaka, Japan

[21] Appl. No.: 982,049

[22] Filed: Nov. 25, 1992

Related U.S. Application Data

[63] Continuation of Ser. No. 360,694, Jun. 2, 1989, abandoned, which is a continuation-in-part of Ser. No. 122,801, Nov. 19, 1987, abandoned.

[30] Foreign Application Priority Data

Nov. 19, 1986 [JP] Japan ................... 50-265335

[51] Int. Cl.⁶ ................... A61K 6/083; C08F 230/08
[52] U.S. Cl. ................... 523/118; 523/116; 424/52; 424/57; 424/55; 526/279
[58] Field of Search ................... 523/116, 109, 523/118; 526/279; 424/52, 55, 57

[56] References Cited

U.S. PATENT DOCUMENTS

| | | | |
|---|---|---|---|
| 4,048,300 | 9/1977 | Tomlinson et al. | 424/674 |
| 4,089,830 | 5/1978 | Tizuka et al. | 523/116 |
| 4,342,677 | 8/1982 | Muramotsu et al. | 523/116 |
| 4,388,069 | 6/1983 | Orlowski | 523/116 |
| 4,404,327 | 9/1983 | Crugnola et al. | 525/228 |
| 4,504,231 | 3/1985 | Koblitz et al. | 523/116 |
| 4,515,910 | 5/1985 | Rawls et al. | 523/115 |
| 4,645,662 | 2/1987 | Nakashima et al. | 424/674 |
| 4,826,893 | 5/1989 | Yamazaki et al. | 523/115 |
| 5,015,467 | 5/1991 | Smitherman | 424/441 |

*Primary Examiner*—Peter F. Kulkosky
*Attorney, Agent, or Firm*—Sughrue, Mion, Zinn, Macpeak & Seas

[57] ABSTRACT

A dental adhesive coating base composition comprising a copolymer represented by formula (I) or (II) in an amount of from 5 to 40 wt % based on the total amounts of the composition; and an oral composition comprising at least one of a copolymer represented by formula (I) and a copolymer represented by formula (II) in an amount of from 5 to 40 wt % based on the total amount of the composition, at least one of a phosphoric acid and tartaric acid present in an amount effective to increase the solubility of fluoride in the composition, up to an amount of 6 wt % or less based on the total amount of the composition; a fluorine-containing compound in an amount effective for dental caries prevention; and a volatile nonaqueous solvent are disclosed:

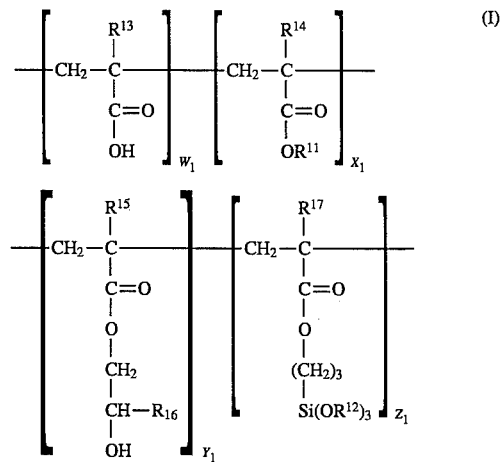

wherein $R^{11}$ represents an alkyl group having from 1 to 10 carbon atoms; $R^{12}$ represents a lower alkyl group having from 1 to 2 carbon atoms, provided that three $R^{12}$ groups must be the same; $R^{13}$, $R^{14}$, $R^{15}$, $R^{16}$ and $R^{17}$, which may be the same or different, each represents a hydrogen atom or a methyl group; $W_1$ is from 5 to 30 wt %; $X_1$ is from 20 to 60 wt %; $Y_1$ is from 20 to 60 wt %; and $Z_1$ is from 0.2 to 20 wt %;

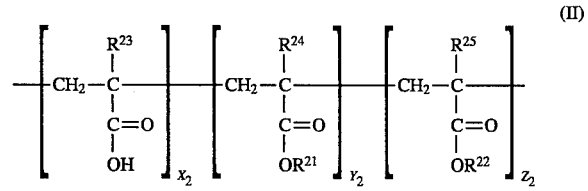

wherein $R^{21}$ and $R^{22}$, which may be the same or different, each represent an alkyl group having from 1 to 10 carbon atoms; $R^{23}$, $R^{24}$, and $R^{25}$, which may be the same or different, each represent a hydrogen atom or a methyl group, provided that at least one of the groups $R^{21}$ and $R^{22}$, and $R^{24}$ and $R^{25}$, respectively, are different from each other; $X_2$ is from 5 to 80 wt %; $Y_2$ is from 10 to 95 wt %; and $Z_2$ is from 0 to 85 wt %.

16 Claims, No Drawings

DENTAL ADHESIVE COATING BASE COMPOSITION AND ORAL COMPOSITION

This is a Continuation of application Ser. No. 07/360,694 filed Jun. 2, 1989 which is a Continuation-In-Part of application Ser. No. 07/122,801 abandoned.

FIELD OF THE INVENTION

The present invention relates to a novel dental adhesive coating base composition exhibiting good adhesion to the teeth, as well as an oral composition capable supplying fluorine to the teeth.

BACKGROUND OF THE INVENTION

Fluorine has been known as a substance which acts on the teeth to enhance the acid-resistance of the enamel, thereby reducing the incidence of dental caries. Conventionally, fluoride compounds such as sodium fluoride, stannous fluoride, and sodium monofluorophosphate are incorporated as fluorine sources in various oral compositions such as dentifrices, mouthrinses, and coating agents in such a way that they act on the surface of teeth, thereby allowing fluorine to exhibit its dental caries preventing effects.

Recent studies have reported that fluorine treatment applied in the early stage of dental caries accelerates remineralization, i.e., restoration of affected teeth to sound ones.

Fluorine-containing dentifrices, mouthrinses, and coating agents have the advantage of easy applicability but their retention in the mouth is not satisfactorily long and the period of time over which fluorine acts on the teeth is insufficiently short. Thus, the uptake of fluorine by the teeth is not high enough to warrant the intended efficacy. Since conventional dental caries-preventing fluorine coating agents employ water-soluble fluorides and are usually formulated in water-soluble dosage forms, they are unable to be retained in the mouth for a satisfactorily long period of time.

Methods have been attempted to improve the oral retention of fluorides by using thickening or gelling water-soluble high molecular weight compounds or by dispersing the fluoride in natural resins, but even such modified agents are unable to be retained in the mouth no more than several hours.

Methyl methacrylate based polymers and bis-GMA based polymers have been known for use as dental compositions such as fissure sealants and dental adhesives. These polymers are used after polymerization and curing having taken place in the mouth, such as by polymerization at ambient temperatures in the presence of benzoyl peroxide or tertiary amines, or by polymerization reaction initiated by ultraviolet or visible ray. In such in situ polymerization methods, some monomers will inevitably remain unreacted and cause deleterious effects to the patient. Furthermore, their applicability is poor because two pastes have to be mixed together or exposure to light is necessary to initiate the polymerization reaction. In addition to this poor applicability, the monomers are so unstable that they have a tendency to become sticky or solidify during prolonged storage, thereby failing to warrant the quality of the product.

SUMMARY OF THE INVENTION

An object of the present invention is to provide a dental adhesive coating base composition which is free from the aforementioned problems of the prior art and which exhibits markedly strong adhesion to the surfaces teeth.

Another object of the present invention is to provide an oral composition which attains markedly strong adhesion to the tooth surfaces and which permits fluoride ions to act on the teeth for a satisfactorily extended period of time.

These and other objects of the present invention will become apparent from the following description.

In order to attain the above objects, the present inventors have conducted intensive studies and have accomplished the present invention.

In one aspect, the present invention provides a dental adhesive coating base composition comprising a copolymer represented by formula (I) in an amount of from 5 to 40 wt % based on the total amount of the composition:

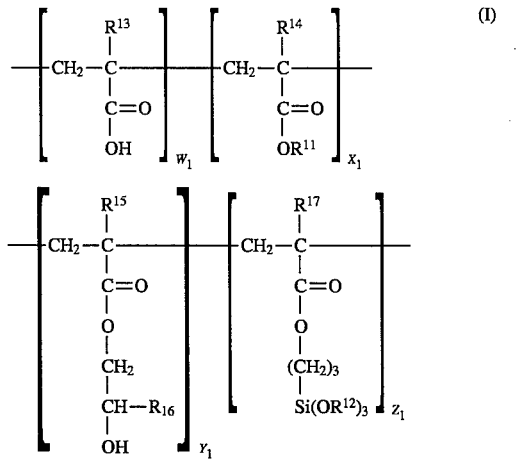

wherein $R^{11}$ represents an alkyl group having from 1 to 10 carbon atoms; $R^{12}$ represents a lower alkyl group having from 1 to 2 carbon atoms, provided that three $R^{12}$ groups must be the same; $R^{13}$, $R^{14}$, $R^{15}$, $R^{16}$ and $R^{17}$, which may be the same or different, each represents a hydrogen atom or a methyl group; $W_1$ is from 5 to 30 wt %; $X_1$ is from 20 to 60 wt %; $Y_1$ is from 20 to 60 wt %; and $Z_1$ is from 0.2 to 20 wt %. Each repeating unit in formula (I) may be composed of two or more kinds of repeating units.

In another aspect, the present invention provides a dental adhesive coating base composition comprising a copolymer represented by formula (II) in an amount of from 5 to 40 wt % based on the total amount of the composition:

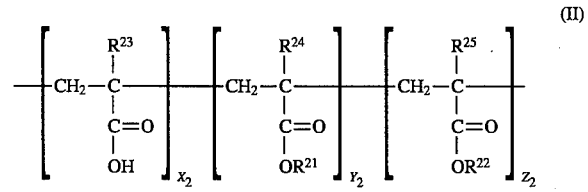

wherein $R^{21}$ and $R^{22}$, which may be the same or different, each represent an alkyl group having from 1 to 10 carbon atoms; $R^{23}$ $R^{24}$ and $R^{25}$ which may be the same or different, each represent a hydrogen atom or a methyl group, provided that at least one of the groups $R^{21}$ and $R^{22}$, and $R^{24}$ and $R^{25}$, respectively, are different from each other; $X_2$ is from 5 to 80 wt % $Y_2$ is from 10 to 95 wt % and $Z_2$ is from 0 to 85 wt %. Each repeating unit in formula (II) may be composed of two or more kinds of repeating units.

In a further aspect, the present invention provides an oral composition comprising at least one of a copolymer represented by formula (I) and a copolymer represented by formula (II) in an amount of from 5 to 40 wt % based on the total amount of the composition; at least one of a phosphoric acid and tartaric acid present in an amount effective to increase the solubility of fluoride in the composition, up to an amount of 6 wt % or less based on the total amount of the composition; a fluorine-containing compound in an amount effective for dental caries prevention; and a volatile non-aqueous solvent.

DETAILED DESCRIPTION OF THE INVENTION

According to the present invention, an acrylic copolymer represented by formula (I) and/or an acrylic copolymer represented by formula (II), a dental adhesive coating base composition is obtained which provides a uniform and highly water-resistant film strongly adhering on the teeth. By using these acryric copolymers, an oral composition is obtained which provides a uniform and highly water-resistant film strongly adhering to the teeth while permitting the fluoride to act on the teeth for a satisfactorily extended period of time.

The monomers used for preparing the acrylic copolymer represented by formula (I) may be selected from those which are identified as the monomeric repeating units in formula (I), and they include: acrylic acid or methacrylic acid; alkyl acrylates or alkyl methacrylates; hydroxyalkyl acrylates or hydroxyalkyl methacrylates; and acryloxypropyl trialkoxysilanes or methacryloxypropyl trialkoxysilanes.

Examples of the alkyl acrylates or the alkyl methacrylates include methyl acrylate, methyl methacrylate, ethyl acrylate, ethyl methacrylate, butyl methacrylate acrylate, 2-ethylhexyl acrylate, and 2-ethylhexyl methacrylate. preferred. examples thereof include methyl methacrylate and butyl methacrylate.

Examples of the hydroxyalkyl acrylates or the hydroxyalkyl methacrylates include hydroxyethyl acrylate, hydroxyethyl methacrylate, hydroxypropyl acrylate, and hydroxypropyl methacrylate. Preferred examples thereof include hydroxyethyl methacrylate.

Examples of the acryloxypropyl trialkoxysilanes or the methacryloxypropyl trialkoxysilanes include acryloxypropyl triethoxysilane, methacryloxypropyl trimethoxysilane, and methacryloxypropyl triethoxysilane. Preferred examples thereof include methacryloxypropyl trimethoxysilane.

These monomers may be present in the acrylic copolymer represented by formula (I) in the following weight proportions acrylic acid or methacrylic acid in an amount of from 5 to 30 wt %, preferably from 10 to 20 wt % ($W_1$); the alkyl acrylate or alkyl methacrylate in an amount of from 20 to 60 wt %, preferably from 25 to 40 wt % ($X_1$); the hydroxyalkyl acrylate or hydroxyalkyl methacrylate in an amount of from 20 to 60 wt %, preferably from 30 to 50 wt % ($Y_1$); and the acryloxypropyl trialkoxysilane or methacryloxypropyl trialkoxysilane in an amount of from 0.2 to 20 wt %, preferably from 1 to 10 wt % ($Z_1$).

The total amount of the acrylic acid or methacrylic acid and the hydroxyalkyl acrylate or hydroxyalkyl methacrylate, i.e., the sum of $W_1$ and $Y_1$, is preferably 25 wt % or more in view of the solubility of the copolymer in the solvent.

The acrylic copolymer represented by formula (I) preferably has a weight average molecular weight of from $10^3$ to $10^6$, more preferably from $1\times10^4$ to $3\times10^5$.

The monomer used for preparing the acrylic copolymer represented by formula (II) may be selected from acrylic acid, methacrylic acid, and one or two kind of alkyl acrylates or alkyl methacrylates. Examples of the alkyl acrylates and the alkyl methacrylates include methyl acrylate, methyl methacrylate, ethyl acrylate, ethyl methacrylate, butyl methacrylate, 2-ethylhexyl acrylate, and 2-ethylhexyl methacrylate. Preferred examples thereof include methyl methacrylate and butyl methacrylate.

These monomers may be present in the acrylic copolymer represented by formula (II) in the following weight proportions: acrylic acid or methacrylic acid in an amount of from 5 to 80 wt %, preferably from 25 to 50 wt % ($X_2$) in view of the solubility of the copolymer in the solvent; the first alkyl acrylate or alkykl methacrylate in amounts of from 10 to 95 wt %, preferably from 25 to 75 wt % ($Y_2$); and the second alkyl acrylate or alkykl methacrylate in amounts of from 0 to 85 wt %, preferably from 0 to 50 wt % ($Z_2$).

The acrylic copolymer represented by formula (II) preferably has a weight average molecular weight of from $10^3$ to $10^6$, more preferably from $1\times10^4$ to $3\times10^5$.

Preferably, the dental- adhesive coating base composition of the present invention further comprises a volatile nonaqueous solvent in an amount of from 60 to 95 wt % based on the total amount of the composition.

The acrylic copolymer used in the oral composition of the present invention is the copolymer represented by of formula (I) or (II) or a mixture of the copolymers represented by formulae (I) and (II).

The acrylic copolymers represented by formulae (I) and (II) which are used in the present invention can be prepared by conventional procedures, e.g., solution polymerization.

The polymerization solvent used in the solution polymerization may be the volatile nonaqueous solvent used in the compositions according to the present invention.

Examples of the polymerization solvent include. methanol, ethanol, isopropanol, acetone, chloroform, and ethyl acetate. Ethanol is preferred since it does not cause any deleterious effects when used in the mouth.

Any conventional radical-forming compounds may be used as a polymerization catalyst and examples thereof include 2,2'-azobisisobutyronitrile, 2,2'-azobis(4-methoxy-2,4-dimethylvaleronitrile), dimethyl 2,2'-azobisisobutyrate, 2,2'-azobis(2,4-dimethylvaleronitrile), benzoyl peroxide, diisopropyl perdicarbonate, and t-butyl perisobutyrate. These polymerization catalysts are generally used in amount of from 0.05 to 2 wt %, preferably from 0.1 to 0.5 wt %, based on the total amount of the monomers.

The polymerization reaction is preferably carried out at a temperature of from 50° to 100° C. and at a temperature not higher than the boiling point of the polymerization solvent.

Since the copolymer solution formed by the reaction described above is substantially free from any unreacted residual monomers, the copolymer solution does not cause deleterious effects during use in the mouth. Therefore, the solution may be satisfactorily used for preparing the compositions of the present invention without being further purified.

The acrylic copolymer of formula (II) and/or (II). is incorporated in the oral composition of the present invention in an amount of from 5 to 40 wt %, preferably from 10 to 30 wt %, based on the total amount of the composition. If the content of the copolymer exceeds 40 wt %, the composition will have an increased viscosity and causes difficulty in forming a uniform coating on the tooth surfaces upon applying. Furthermore, the applicability of the composition is also impaired. If the content of the copolymer is less than 5 wt % based on the composition, it does not have suffcient adhesion force to produce a persistent coat on the tooth surfaces.

Examples of the volatile nonaqueous solvent which may be used in the compositions of the present invention include methanol, ethanol, isopropanol, acetone, chloroform and ethyl acetate. Most preferably, ethanol is used in view of the least deleterious effects upon using in the mouth. The polymerization solvent used may be used for the volatile nonaqueous solvent.

The dental adhesive coating base composition which contains the acrylic copolymer represented formula (I) or (II) may further contain a viscosity modifying agent and other appropriate additives so that it can be used as fissure sealants, orthodontic adhesives or as bonding agents for filling materials such as composite resins. Alternatively, the dental adhesive coating base composition may further contain a pigment or other coloring agents so that it can be used as a dental lacquer. If desired, the composition may be used as a therapeutic agent after incorporating a pharmaceutically active ingredient.

Any of the fluorides which are commonly known to have the ability to increase the resistance of the tooth may be incorporated in the oral composition of the present invention. Specific examples thereof include sodium fluoride, calcium fluoride, stannous fouoride, zinc fluoride, strontium fluoride and sodium monofluorophosphate. Among these fluorides, sodium fluoride is most preferred. These fluorides are preferably incorporated in an amount effective for the purpose of dental caries prevention, which is preferably from 0.001 to 0.02 wt % to the total amount of the composition. More particularly, the fluoride ion concentration range is preferably from 1 ppm to 9,000 ppm (by weight), and, more preferably, the range is from 17 to 4,430 ppm.

The oral composition of the present invention also contains a phosphoric acid and/or tartaric acid, both of which have the ability to increase the solubility of fluoride which is slightly soluble in ethanol. By incorporating the phosphoric acid and/or tartaric acid in the oral composition, the fluoride is solubilized and contained stably in the composition. Examples of the phosphoric acid include not only orthophosphoric acid but also phosphorous acid, metaphosphoric acid, and polyphosphoric acid. The phosphoric acid and/or tartaric acid is preferably incorporated in an amount of 6 wt % or less, preferably from 0.01 to 1 wt %, based on of the total amount of the composition.

The solubilizing effect of the phosphoric acid and tartaric acid as achieved when a fluoride is incorporated in volatile solvents was tested by the following method.

TEST EXAMPLE

A great excess amount of sodium fluoride was added to 20 ml of an ethanol solutions containing varying concentrations (0.1 to 10%) of phosphoric acid or tartaric acid. The contents were heated with shaking at 30° C. for 2 hours, followed by shaking at 20° C. Excess sodium fluoride was filtered off and the concentration of fluoride ions in the filtrate was measured with a fluoride ion electrode. The results are shown in Table 1.

TABLE 1

| Concentration of phosphoric acid or tartaric acid (%) | NaF concentration | |
|---|---|---|
| | Presence of phosphoric acid (ppm) | Presence of tartaric acid (ppm) |
| 0 | 20 | 20 |
| 0.1 | 360 | 240 |
| 0.5 | 1,400 | 1,100 |
| 1 | 2,300 | 2,200 |
| 2 | 3,800 | 4,000 |
| 4 | 6,500 | 6,100 |
| 6 | 5,000 | 6,500 |
| 8 | 4,800 | 5,300 |
| 10 | 4,100 | 4,200 |

As is clear from Table 1, tartaric acid or phosphoric acid present in amounts of from 0 to 6% was effective for increasing the solubility of fluorides. When these acids were present in amounts exceeding 6%, the solubility of the fluoride decreased. In addition, tartaric acid or phosphoric acid present in an amount of more than 6% will inhibit the dissolution of the acrylic copolymers of the present invention in volatile nonaqueous solvents. Therefore, it is preferred that the concentration of tartaric acid and/or phosphoric acid is or less for stable formulation of the composition.

The oral composition of the present invention may be produced by mixing the desired components and making them into solution by conventional procedures, such as by using a vacuum stirrer.

If desired, a pigment, a preservative and some other suitable ingredients may be incorporated in the oral composition of the present invention so that it can be used as an anti-caries agent. When a pigment is incorporated, the area of teeth surface where the composition is applied can be easily identified. The oral composition may be coated on teeth in the early stage of caries so that it produces therapeutic effects by accelerating remineralization. The composition has the additional advantage of convenience and ease of application since a persistent film can be formed very shortly by coating the composition on tooth surfaces with, e.g., a fine brush and drying with air.

The following examples are provided for the purpose of further illustrating the present invention but are in no sense to be taken as limiting. In the following examples, all percents are by weight.

EXAMPLE 1

Sample I-1 of a copolymer represented by formula (I) was prepared by the following procedures.

A 30% ethanol solution containing 5 g of methacrylic acid, 15 g of methyl methacrylate, 25 g of hydroxyethyl mehtacrylate, and 5 g of methacryloxypropyl trimethoxysilane was prepared in a three-necked flask equipped with a thermometer, a reflux condenser and a nitrogen inlet tube. The contents of the flask were degassed by stirring for 1 to 2 hours under a nitrogen stream. Subsequently, 0.25 g of 2'-azobis(2,4dimethylvaleronitrile) was added and polymerization was conducted at 60° C. for 20 hours. Thereafter, 0.2 g of 2'-azobis(2,4-dimethylvaleronitrile) was added, then polymerization was continued at 78° C. for 4 hours until the reaction was completed. The resulting product was diluted with ethanol to make a colorless transparent 20% polymer solution. The copolymer produced was found to have a weight average molecular weight of 12.0×10⁴ by gel permeation chromatography (GPC).

Sample I-2 of a copolymer represented by formula (I) was prepared by the following procedures.

A 30% ethanol solution containing 5 g of methacrylic acid, 15 g of ethyl methacrylate, 25 g of hydroxyethyl mehtacrylate, and 5 g of methacryloxypropyl trimethoxysilane was prepared in a three-necked flask equipped with a thermometer, a reflux condenser and a nitrogen inlet tube. The contents of the flask were degassed by stirring for 1 to 2 hours under a nitrogen stream. Subsequently, 0.25 g of 2'-azobis(2,4-dimethylvaleronitrile) was added and polymerization was conducted at 60° C. for 20 hours. Thereafter, 0.2 g of 2'-azobis(2,4-dimethylvaleronitrile) was added, and then polymerization was continued at 78° C. for 4 hours until the reaction was completed. The resulting product was diluted with ethanol to make a colorless transparent 20% polymer solution. The copolymer produced was found to have a weight average molecular weight of $9.8 \times 10^4$ by gel permeation chromatography (GPC).

Sample I-3 of a copolymer represented by formula (I) was prepared by the following procedures.

A 30% ethanol solution containing 5 g of methacrylic acid, 15 g of butyl methacrylate, 25 g of hydroxyethyl mehtacrylate, and 5 g of methacryloxypropyl trimethoxysilane was prepared in a three-necked flask equipped with a thermometer, a reflux condenser and a nitrogen inlet tube. The contents of the flask were degassed by stirring for 1 to 2 hours under a nitrogen stream. Subsequently, 0.25 g of 2'-azobis(2,4dimethylvaleronitrile) was added and polymerization was conducted at 60° C. for 20 hours. Thereafter, 0.2 g of 2'- azobis (2,4-dimethylvaleronitrile) was added, and then polymerization was continued at 78° C. for 4 hours until the reaction was completed. The resulting product was diluted with ethanol to make a colorless transparent 20% polymer solution. The copolymer produced was found to have a weight average molecular weight of $12.4 \times 10^4$ by gel permeation chromatography (GPC).

Sample I-4 of a copolymer represented by formula (I) was prepared by the following procedures.

A 30% ethanol solution containing 5 g of methacrylic acid, 24 g of ethyl methacrylate, 20 g of hydroxyethyl acrylate, and 5 g of methacryloxypropyl trimethoxysilane was prepared in a three-necked flask equipped with a thermometer, a reflux condenser and a nitrogen inlet tube. The contents of the flask were degassed by stirring for 1 to 2 hours under a nitrogen stream. Subsequently, 0.25 g of 2'-azobis(2,4-dimethylvaleronitrile) was added and polymerization was conducted at 60° C. for 20 hours. Thereafter, 0.2 g of 2'-azobis (2,4-dimethylvaleronitrile) was added, and then polymerization was continued at 78° C. for 4 hours until the reaction was completed. The resulting product was diluted with ethanol to make a colorless transparent 20% polymer solution. The copolymer produced was found to have a weight average molecular weight of $10.2 \times 10^4$ by gel permeation chromatography (GPC).

Sample I-5 of a copolymer represented by formula (I) was prepared by the following procedures.

A 30% ethanol solution containing 7.5 g of methacrylic acid, 15 g of butyl methacrylate, 25 g of hydroxyethyl mehtacrylate, and 2.5 g of methacryloxypropyl trimethoxysilane was prepared in a three-necked flask equipped with a thermometer, a reflux condenser and a nitrogen inlet tube. The contents of the flask were degassed by stirring for 1 to 2 hours under a nitrogen stream. Subsequently, 0.2 g of benzoyl peroxide was added and polymerization was conducted at 75 to 78° C. for 20 hours. Thereafter, 0.2 g benzoyl peroxide was added, and then polymerization was continued at 78° C. for 4 hours until the reaction was completed. The resulting product was diluted with ethanol to make a colorless transparent 20% polymer solution. The copolymer produced was found to have a weight average molecular weight of $20.2 \times 10^4$ by gel permeation chromatography (GPC).

Sample I-6 of a copolymer represented by formula (I) was prepared by the following procedures.

A 30% ethanol solution containing 5 g of methacrylic acid, 15 g of butyl-methacrylate, 25 g of hydroxyethyl mehtacrylate, and 2.5 g of methacryloxypropyl trimethoxysilane was prepared in a three-necked flask equipped with a thermometer, a reflux condenser and a nitrogen inlet tube. The contents of the flask were degassed by stirring for 1 to 2 hours under a nitrogen stream. Subsequently, 0.475 g of 70% t-butyl perisobutyrate was added and polymerization was conducted at 75 to 78° C. for 20 hours. Thereafter, 0.475 g of t-butyl perisobutyrate was added, and then polymerization was continued at 78° C. for 4 hours until the reaction was completed. The resulting product was diluted with ethanol to make a colorless transparent 20% polymer solution. The copolymer produced was found to have a weight average molecular weight of $18.3 \times 10^4$ by gel permeation chromatography (GPC).

Coating base compositions within the scope of the present invention thus prepared, i.e., 20% ethanol solutions of Samples I-1 to I-6 each were applied to cleaned and dried surfaces of bovine teeth. The treated teeth were dried at ambient temperature for 10 minutes and immersed in 20 ml of distilled water at 37° C. for 10 days. Visual inspection indicated that the coating on the surfaces of bovine teeth remained intact because of its satisfactorily high water resistance.

EXAMPLE 2

Impacted front teeth of cows 2 to 3 years of age were embedded in a selfcuring resin (φ1×2 cm) exposing by one half the height of the margo incicivus of the corona dentis. A polyvinylidene chloride sheet with a small hole (diameter: 3 mm) was inserted between the teeth so as to contact the teeth each other. The 20 % ethanol solutions of the copolymer samples (I-1 to I-6) obtained in Example each were poured between the teeth so that they were adhered each other. The teeth were then left to stand in air at room temperature for 24 hours and subjected to a tensile test with an autograph for measuring of the adhesion strength of each sample. The results obtained are shown in Table 2 in terms of the average of 5 measurements.

TABLE 2

| Sample | Adhesive strength (kg/cm²) |
|---|---|
| I-1 | 14.5 |
| I-2 | 14.5 |
| I-3 | 13.8 |
| I-4 | 15.0 |
| I-5 | 16.0 |
| I-6 | 13.4 |

The results in Table 2 indicate that the compositions prepared in accordance with the present invention provided satisfactory adhesion strength as dental coating base compositions.

EXAMPLE 3

Sample II-1 of a copolymer represented by formula (II) was prepared by the following procedures.

A 30% ethanol solution containing 25 g of methacrylic acid, and 25 g of methyl methacrylate was prepared in a three-necked flask equipped with a thermometer, a reflux condenser and a nitrogen inlet tube. The contents of the flask were degased by stirring for 1 to 2 hours under a nitrogen stream. Subsequently, 0.5 g of 2,2'-azobisisobutyronitrile was added and polymerization was conducted at 70° C. for 20 hours. Thereafter, 0.2 g of 2,2'-azobisisobutyronitrile was added, and then polymerization was continued at 78° C. for 4 hours until the reaction was completed. The resulting product was diluted with ethanol to make a colorless transparent 20% polymer solution. The copolymer produced was found to have a weight average molecular weight of $4.1 \times 10^4$ by gel permeation chromatography (GPC).

Sample II-2 of a copolymer represented by formula (II) was prepared by the following procedures.

A 30% ethanol solution containing 15 g of methacrylic acid, 20 g of methyl methacrylate, and 15 g of ethyl acrylate was prepared in a three-necked flask equipped with a thermometer, a reflux condenser and a nitrogen inlet tube. The contents of the flask were degased by stirring for 1 to 2 hours under a nitrogen stream. Subsequently, 0.25 g of 2'-azobis(2,4dimethylvaleronitrile) was added and polymerization was conducted at 60° C. for 20 hours. Following additional supply of 8.2 g of 2'-azobis(2,4-dimethylvaleronitrile) was added, and then polymerization was continued at 78° C. for 4 hours until the reaction was completed. The resulting product was diluted with ethanol to make a colorless transparent 20% polymer solution. The copolymer produced was found to have a weight average molecular weight of $6.7 \times 10^4$ by gel permeation chromatography (GPC).

Sample II-3 of a copolymer represented by formula. (II) was prepared by the following procedures.

A 30% ethanol solution containing 15 g of methacrylic acid, 20 g of methyl methacrylate, and 15 g of butyl methacrylate was prepared in a three-necked flask equipped with a thermometer, a reflux condenser and a nitrogen inlet tube. The contents of the flask were degassed by stirring for 1 to 2 hours under a nitrogen stream. Subsequently, 0.25 g of 70% t-butyl perisobutyrate was added and polymerization was conducted at 60° C. for 20 hours. Thereafter, 0.2 g of 70% t-butyl perisobutyrate was added, and then polymerization was continued at 78° C. for 4 hours until the reaction was completed. The resulting product was diluted with ethanol to make a colorless transparent 20% polymer solution. The copolymer produced was found to have a weight average molecular weight of $7.5 \times 10^4$ by gel permeation chromatography (GPC).

Coating base compositions within the scope of the present invention thus prepared, i.e., 20% ethanol solution of Samples II-1 to II-3 each were applied to cleaned and dried surfaces of bovine teeth. The treated teeth were dried at ambient temperature for 10 minutes and immersed in 20 ml of distilled water at 37° C. for 10 days. Visual inspection indicated that the coating on the surfaces of bovine teeth remained intact because of its satisfactorily high water resistance.

EXAMPLE 4

Impacted front teeth of cows 2 to 3 aged were embedded in a selfcuring resin ($\phi 1 \times 2$ cm) exposing by one half the height of the margo incicivus of the corona dentis. A polyvinylidene chloride sheet with a small hole (diameter: 3 mm) was inserted between the teeth so as to contact the teeth each other. The 20 % ethanol solutions of the copolymer samples (II-1 to II-3) each were poured between the teeth so that they were adhered each other. The teeth were then left to stand in air at room temperature for 24 hours and subjected to a tensile test with an autograph for measuring the adhesion strength of each sample. The results obtained are shown in Table 2 in terms of the average of 5 measurements.

TABLE 3

| Sample | Adhesive strength (kg/cm$^2$) |
| --- | --- |
| II-1 | 17.8 |
| II-2 | 7.3 |
| II-3 | 6.5 |

The results in Table 3 indicate that the compositions prepared in accordance with the present invention provided satisfactory adhesion strength as dental coating base compositions.

EXAMPLE 5

Using the copolymers Samples I-1, I-4, II-1, and II-3 prepared in Examples 1 and 3, transparent liquid oral compositions (Samples A to G) were prepared by mixing the ingredients listed in Table 4 and dissolving them in ethanol by using a vacuum stirrer.

TABLE 4

| Components | Amount | | | | | | |
| --- | --- | --- | --- | --- | --- | --- | --- |
|  | A (%) | B (%) | C (%) | D (%) | E (%) | F (%) | G (%) |
| Copolymer II-1 | 15.0 | 15.0 | — | 15.0 | 7.5 | — | — |
| Copolymer II-3 | — | — | — | — | — | 15.0 | — |
| Copolymer I-1 | — | — | 15.0 | — | 7.5 | — | — |
| Copolymer I-4 | — | — | — | — | — | — | 15.0 |
| Sodium fluoride | 0.001 | 0.01 | 0.001 | 0.001 | 0.001 | 0.001 | 0.001 |
| Phosphoric acid | 0.1 | 0.1 | — | — | — | 0.1 | 0.1 |
| Tartaric Acid | — | — | 0.1 | 0.1 | 0.1 | — | — |
| Ethanol | balance | balance | balance | balance | balance | balance | balance |

The adhesion strength of thus prepared oral compositions Samples A to G were measured in the same manner as in Example 2. The results obtained are shown in Table 5.

TABLE 5

| Sample | Adhesive strength (kg/cm$^2$) |
|---|---|
| A | 15.8 |
| B | 13.6 |
| C | 14.0 |
| D | 16.2 |
| E | 13.9 |
| F | 6.1 |
| G | 15.2 |

The results in Table 5 indicate that the oral compositions in accordance with the present invention provide satisfactory adhesion strength as oral compositions.

2 g of the oral compositions Samples A to G each were poured into 50 ml wide mouth bottle, and the volatile component (ethanol) was removed at room temperature so as to prepare a resin layer having a surface area of 10 cm$^2$ inside the bottle. 50 ml of distilled water was poured into the bottle and then allowed to stand for one week at room temperature. Thereafter, the amount of fluoride ions eluted from the resin layer with the distilled water was measured by using a fluoride ion electrode. The results obtained are shown in Table 6 in terms of the average of 3 measurements.

TABLE 6

| Sample | Fluoride ion amount (μg) |
|---|---|
| A | 1.4 |
| B | 4.6 |
| C | 5.1 |
| D | 1.4 |
| E | 8.1 |
| F | 1.6 |
| G | 3.1 |

The results in Table 6 indicate that fluoride ions were eluted from all the samples of the oral compositions in accordance with the present invention, thus it is apparent that the oral compositions sufficiently supply fluoride ions to the teeth.

Blocks (7 mm × 5 mm) of the enamel of bovine teeth were immersed for 3 days in a solution of 0.1M lactic acid solution containing 5 mM of Ca and 3 mM of P so as to produce an artificial lesion at the early stage of caries. Samples A and B of the oral composition were applied to these blocks to form a transparent coating on each block.

Subsequently, the blocks were then immersed in artifical saliva (pH, 7.0) for 2 days at 37° C. and then the coatings of Samples A and B were removed. Thereafter, the blocks were immersed in an acetate buffer solution for 6 hours at 37° C. and the amount of Ca which was eluted from the enamel with the buffer solution was measured. As a control experiment, the same procedures as above were conducted except that the oral composition of the present invention was not coated. The results obtained are shown in Table 7.

TABLE 7

| Sample | Amount of eluted Ca (mM/cm$^2$) |
|---|---|
| Control | 7.5 |
| A | 2.4 |
| B | 2.6 |

As is clear from the results shown in Table 7, when the oral composition of the present invention is coated, the amount of Ca eluted from the artificial carious lesion is reduced in comparison to the control experiment without the coating of the oral composition. In other words, the carious enamel treated with the oral composition of the present invention regained its acid resistance and indicated tendency of restoration to sound enamel. This increase in the resistance of the tooth was caused by the deposition of fluorine into the tooth enamel from the oral composition of the present invention, thereby providing caries-preventing effects.

EXAMPLE 6

20 ml of 99.5% ethanol containing various amounts of acids and copolymers as shown in Table 8 below was placed in vessels, and 0.2 g of NaF was added to each vessel. The mixtures in the vessels were shaken for 2 hours at room temperature. The supernatant was collected by centrifugation, and the fluoride ion concentration thereof was determined by means of a fluoride ion electrode. The results are shown in Table 8 below.

TABLE 8

| Acid | | Copolymer II-3 | Fluoride ion |
|---|---|---|---|
| Kind | Conc. (%) | Conc. (%) | Conc. (ppm) |
| — | 0 | 5 | 16 |
| — | 0 | 20 | 13 |
| Phosphoric acid | 0.01 | 5 | 23 |
| Phosphoric acid | 0.01 | 20 | 34 |
| Phosphoric acid | 1 | 5 | 1,410 |
| Phosphoric acid | 1 | 20 | 882 |
| Phosphoric acid | 6 | 5 | 2,020 |
| Phosphoric acid | 6 | 20 | 1,430 |
| Tartaric acid | 0.01 | 5 | 17 |
| Tartaric acid | 0.01 | 20 | 19 |
| Tartaric acid | 1 | 5 | 1,630 |
| Tartaric acid | 1 | 20 | 823 |
| Tartaric acid | 6 | 5 | 4,430 |
| Tartaric acid | 6 | 20 | 3,640 |
| Methacrylic acid | 0.01 | 5 | 20 |
| Methacrylic acid | 0.01 | 20 | 22 |
| Methacrylic acid | 1 | 5 | 19 |
| Methacrylic acid | 1 | 20 | 9 |
| Methacrylic acid | 6 | 5 | 35 |
| Methacrylic acid | 6 | 20 | 35 |

As is clear from the results in Table 8, tartaric acid or phosphoric acid was effective for increasing the solubility of fluorides in the presence of the copolymer.

In the above comparative testing, when the copolymer concentration was increased to 40%, the experiment was impossible, because the mixture became too viscous for the measurement of the fluoride ion. That is, when ethanol without tartaric or phosphoric acid was used, the fluorides were not dissolved in ethanol, and thus the composition was not obtained. However, the composition of the present invention having a copolymer concentration of 40% was obtained by firstly dissolving fluorides in an ethanol solution of tartaric acid or phosphoric acid, and then dissolving the copolymer therein.

Ethanol was used as the non-aqueous volatile solvent in the above experiments. However, solvents disclosed herein other than ethanol behave similarly to ethanol for purposes of this invention.

As described in the foregoing, the dental adhesive coating base composition of the present invention does not contain any unreacted monomers which cause deleterious effects on the oral environment. In addition, this composition exhibits strong adhesion to the tooth and retains strong adhesion force to the tooth surfaces even in water or saliva. If this composition is used as a fissure sealant, it may simply be coated on dried surfaces of teeth with a cotton pilot, thereby forming a uniform film on the tooth surfaces. In this respect, the oral composition of the present invention can be applied easily in comparison to the conventional compositions which require polymerization in the mouth. The composition of the present invention has the additional advantage that it warrants high quality since it is free from the problem of deterioration or solidification during storage.

Thus, the oral composition of the present invention has superior adhesion to the tooth and high resistance to water, for a prolonged period of time. In addition, the composition contains fluorine in a stable form so that if it is applied to the surface of teeth, it forms a film from which fluorine acts on the enamel persistently. Therefore, by applying the oral composition of the present invention to the teeth, both caries prevention and increase in the resistance of the teeth can be achieved. As a further advantages, since the fluoride in the oral composition is carried away by saliva only in a small amount, the concentration of fluoride required to be incorporated to attain the caries-preventing effect can be reduced in comparison to the conventional product.

While the invention has been described in detail and with reference to specific examples thereof, it will be apparent to one skilled in the art that various changes and modifications can be made therein without departing from the spirit and scope thereof.

What is claimed is:

1. A dental adhesive coating base composition comprising a copolymer represented by formula (I) in an amount of from 5 to 40 wt % based on the total amount of said dental adhesive coating base composition and a volatile nonaqueous solvent in an amount of from 60 to 95 wt % based on the total amount of said dental adhesive coating base composition:

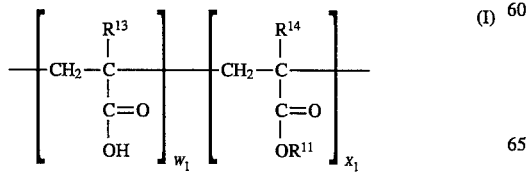

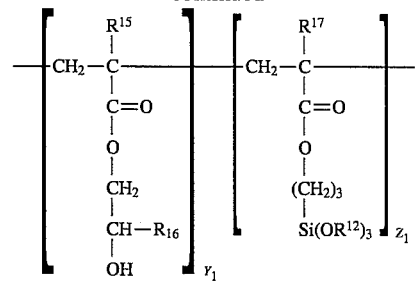

wherein $R^{11}$ represents an alkyl group having from 1 to 10 carbon atoms; $R^{12}$ represents a lower alkyl group having from 1 to 2 carbon atoms provided that three $R^{12}$ groups are the same; $R^{13}$, $R^{14}$, $R^{15}$, $R^{16}$, and $R^{17}$, which may be the same or different, each represents a hydrogen atom or a methyl group; $W_1$ is from 5 to 30 wt %; $X_1$ is from 20 to 60 Wt%; $Y_1$ from 20 to 60 wt %; and $Z_1$ is from 0.2 to 20 wt %; and wherein said copolymer is water-insoluble and soluble in the volatile nonaqueous solvent, and said volatile nonaqueous solvent is ethanol.

2. A dental adhesive coating base composition as claimed in claim 1, wherein $R^{11}$ represents a methyl group or a butyl group; $R^{12}$, $R^{14}$, $R^{15}$, and $R^{17}$ each represents a methyl group; and $R^{16}$ represents a hydrogen atom.

3. A dental adhesive coating base composition as claimed in claim 1, wherein $R^{24}$ represents a methyl group; and $R^{21}$ represents a methyl group or a butyl group.

4. A dental adhesive coating base composition as claimed in claim 1, wherein the weight average molecular weight of said copolymer represented by formula (I) is in the range of from $1\times10^4$ to $3\times10^5$.

5. A dental adhesive coating base composition as claimed in claim 1, wherein $W_1$ is from 10 to 20 wt %; $X_1$ is from 25 to 40 wt %; $Y_1$ is from 30 to 50 wt %; and $Z_1$ is from 1 to 10 wt %.

6. A dental coating composition comprising a copolymer represented by formula (I) in an amount of from 5 to 40 wt % based on the total amount of said dental coating composition; at least one of phosphoric acid and tartaric acid are present in said dental coating composition in an amount of from 0.01 to 1 wt % based on the total amount of said dental coating composition, said amount being up to 6 wt % based on the total amount of said dental coating composition; sodium fluoride in an amount effective for dental caries prevention; and a volatile nonaqueous solvent:

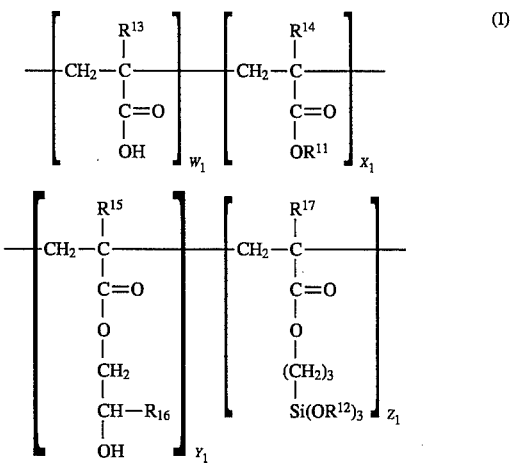

wherein $R^{11}$ represents an alkyl group having from 1 to 10 carbon atoms; $R^{12}$ represents a lower alkyl group having from 1 to 2 carbon atoms provided that three $R^{12}$ groups are the same; $R^{13}$, $R^{14}$, $R^{15}$, $R^{16}$, and $R^{17}$, which may be the same or different, each represents a hydrogen atom or a methyl group; $W_1$ is from 5 to 30 wt %; $X_1$ is from 20 to 60 wt %; $Y_1$ is from 20 to 60 wt %; and $Z_1$ is from 0.2 to 20 wt %; and wherein said copolymer is water-insoluble and soluble in the volatile nonaqueous solvent, and said volatile nonaqueous solvent is ethanol.

7. A dental coating composition as claimed in claim 6, wherein said sodium fluoride is incorporated in said dental coating composition in an amount of from 0.001 to 0.02 wt % based on the total amount of said dental coating composition.

8. A dental coating composition as claimed in claim 6, wherein said sodium fluoride is incorporated in said dental coating composition in an amount so as to provide a fluoride-ion concentration of from 1 to 9,000 ppm.

9. A dental coating composition as claimed in claim 8, wherein said sodium fluoride is incorporated in said dental coating composition in an amount so as to provide a fluoride-ion concentration of from 17 to 4,430 ppm.

10. A dental coating composition as claimed in claim 6, wherein said at least one of phosphoric acid and tartaric acid is incorporated in said dental coating composition in an amount of from 0.5 to 6 wt % based on the total amount of said dental coating composition.

11. A copolymer represented by formula (I):

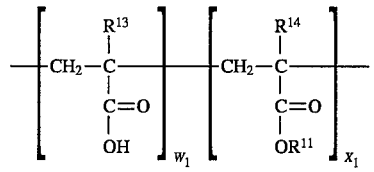

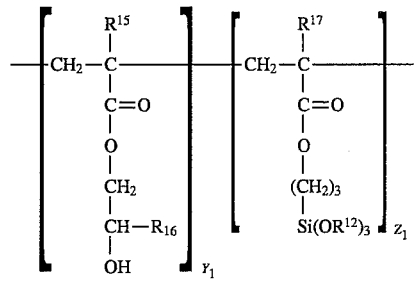

wherein $R^{11}$ represents an alkyl group having from 1 to 10 carbon atoms; $R^{12}$ represents a lower alkyl group having from 1 to 2 carbon atoms provided that three $R^{12}$ groups are the same; $R^{13}$, $R^{14}$, $R^{15}$, $R^{16}$, and $R^{17}$, which may be the same or different, each represents a hydrogen atom or a methyl group; $W_1$ is from 5 to 30 wt %; $X_1$ is from 20 to 60 wt %; $Y_1$ is from 20 to 60 wt %; and $Z_1$ is from 0.2 to 20 wt %, and wherein said copolymer represented by formula (I) has a weight-average molecular weight of from $1\times10^3$ to $1\times10^6$.

12. A dental adhesive coating base composition as claimed in claim 1, wherein said copolymer represented by formula (I) has a weight average molecular weight of from $1\times10^4$ to $1\times10^6$.

13. A dental adhesive coating base composition as claimed in claim 1, wherein said copolymer represented by formula (I) has a weight average molecular weight of from $1\times10^4$ to $3\times10^5$.

14. A dental coating composition as claimed in claim 6, wherein said copolymer represented by formula (I) has a weight average molecular weight of from $1\times10^3$ to $1\times10^6$.

15. A dental coating composition as claimed in claim 6, wherein said copolymer represented by formula (I) has a weight average molecular weight of from $1\times10^4$ to $3\times10^5$.

16. A copolymer as claimed in claim 1, wherein said copolymer represented by formula (I) has a weight average molecular weight of from $1\times10^4$ to $3\times10^5$.

* * * * *